(12) United States Patent
Georgiou et al.

(10) Patent No.: US 9,759,562 B2
(45) Date of Patent: Sep. 12, 2017

(54) HYBRID MEMS MICROFLUIDIC GYROSCOPE

(71) Applicants: Julius Georgiou, Nicosia (CY); Charalambos Michael Andreou, Nicosia (CY)

(72) Inventors: Julius Georgiou, Nicosia (CY); Charalambos Michael Andreou, Nicosia (CY)

(73) Assignee: University of Cyprus, Nicosia (CY)

( * ) Notice: Subject to any disclaimer, the term of this patent is extended or adjusted under 35 U.S.C. 154(b) by 0 days.

(21) Appl. No.: 14/425,153

(22) PCT Filed: Sep. 4, 2013

(86) PCT No.: PCT/IB2013/002555
§ 371 (c)(1),
(2) Date: Mar. 2, 2015

(87) PCT Pub. No.: WO2014/037808
PCT Pub. Date: Mar. 13, 2014

(65) Prior Publication Data
US 2015/0260518 A1 Sep. 17, 2015

Related U.S. Application Data

(60) Provisional application No. 61/696,318, filed on Sep. 4, 2012.

(51) Int. Cl.
*A61B 5/00* (2006.01)
*G01C 19/14* (2006.01)
*G01P 15/00* (2006.01)
*G01P 15/03* (2006.01)
*A61N 1/36* (2006.01)
(Continued)

(52) U.S. Cl.
CPC ............ *G01C 19/14* (2013.01); *A61B 5/1121* (2013.01); *A61B 5/4023* (2013.01); *A61B 5/6847* (2013.01); *A61N 1/36032* (2013.01); *G01P 3/26* (2013.01); *G01P 15/006* (2013.01);
(Continued)

(58) Field of Classification Search
CPC ..... A61B 5/686; A61B 5/1121; A61B 5/4023; A61B 5/6847; A61N 1/0541; A61N 1/36032; H01L 2924/1461; B81B 2203/01148; B81B 2201/0264; G01C 19/14
See application file for complete search history.

(56) References Cited

U.S. PATENT DOCUMENTS

3,693,460 A * 9/1972 Saadeh .................. E21B 47/00
73/514.03
8,759,990 B2 * 6/2014 Huffman ............. H01L 41/1138
290/1 R
(Continued)

*Primary Examiner* — Max Hindenburg
(74) *Attorney, Agent, or Firm* — Bryan W. Bockhop; Bockhop Intellectual Property Law, LLC (57) ABSTRACT

A hybrid MEMS microfluidic gyroscope is disclosed. The hybrid MEMS microfluidic gyroscope may include a micro-machined base enclosure having a top fluid enclosure, a fluid sensing enclosure and a bottom fluid enclosure. The hybrid MEMS microfluidic gyroscope may include a plurality of cantilevers disposed within the bottom semi-circular portion of the micro-machined base enclosure or a single membrane disposed within the bottom semi-circular portion of the micro-machined base enclosure.

10 Claims, 7 Drawing Sheets

(51) Int. Cl.
*G01P 3/26* (2006.01)
*G01P 15/08* (2006.01)
*G01P 15/14* (2013.01)
*A61B 5/11* (2006.01)

(52) U.S. Cl.
CPC ........ *G01P 15/038* (2013.01); *G01P 15/0888* (2013.01); *G01P 15/14* (2013.01)

(56) References Cited

U.S. PATENT DOCUMENTS

| | | | | |
|---|---|---|---|---|
| 8,864,287 | B2* | 10/2014 | Huffman | B41J 2/14427 347/11 |
| 8,877,537 | B2* | 11/2014 | Mao | B81C 1/00293 438/52 |
| 2010/0281978 | A1* | 11/2010 | Chang | G01P 15/006 73/514.11 |

* cited by examiner

HYBRID MEMS MICROFLUIDIC GYROSCOPE

This application claims priority to U.S. Provisional Application 61/696,318 filed on Sep. 4, 2012, the entire disclosure of which is incorporated by reference.

BACKGROUND OF THE INVENTION

Field of the Invention

The present invention is a micro electro-mechanical system or MEMS gyroscope. More specifically, the present invention is a hybrid MEMS microfluidic gyroscope.

Description of the Related Art

Low power, low cost, small-footprint gyroscope development has been predominantly driven by the mobile phone and gaming industry. However the power and reliability requirement, in these industries, is far less stringent than those required for implantable devices. In vestibular prototypes, the gyroscope tends to consume most of the supplied power, and as such, the lack of a suitable off-the-shelf gyroscope may be holding back a fully implantable vestibular prosthesis. State-of-the-art gyroscopes avoid utilizing large masses by vibrating small masses and exploiting the Coriolis Effect. Vibrating structures need voltages as high as approximately forty volts to electro-statically stimulate the vibration. In addition, vibrating these structures at hundreds of kilohertz, for over a decade, is likely to cause fatigue and premature failure of the sensor. Although non-vibratory structures have been explored, so far their complexity has impeded their advance into mainstream products and the reliability of a large solid mass suspended in vacuum on thin suspension beams is questionable, especially if dropped on a hard surface. Therefore, there is a clear need for a much lower power angular rate sensor that may reliably operate over the remaining lifetime of a patient.

BRIEF SUMMARY OF THE INVENTION

The present invention is a hybrid electro-mechanical system gyroscope. More specifically, the present invention is a hybrid micro electro-mechanical system gyroscope or MEMS gyroscope. The present invention is based on the same mechanisms utilized in natural semicircular canals, whereby the inertial mass of a fluid is utilized to deform a sensing structure. The presented gyroscope has been fabricated in a commercially available MEMS process. This process allows for micro-fluidic channels to be implemented in etched glass layers, which sandwich a bulk micro-machined silicon substrate, containing the sensing structures. The proposed approach has exhibited similar device performance to its natural counterpart, while maintaining an extremely low-energy budget, by not utilizing a continually-excited vibrating mass, as is popular in commercial angular rate sensors. Furthermore it is expected that it will have a longer lifespan than today's gyroscopic devices, since the sensing element is not continually being excited at hundreds of kilohertz.

The present invention is a hybrid MEMS microfluidic gyroscope that includes a micro-machined, closed-shape, fluidic-mass filled, distorted tubular enclosure, which predominantly occupies an arbitrary plane or one or more parallel planes with a plurality of holes made through a material suitable for constructing sensing structures with commonly used MEMS techniques, linking the portions of the closed shape on different planes. The fluidic mass is dispersed through an aperture disposed on the micro-machined base enclosure and flows within the top semi-circular portion and the bottom semi-circular portion of the micro-machined base enclosure via the holes. The present invention also includes a plurality of piezo-resistors disposed within the middle layer, the piezo-resistors are deformed by the fluidic mass, the fluidic mass prevents gravitational forces asserted onto the hybrid MEMS microfluidic gyroscope from affecting the piezo-resistors and a plurality of cantilevers disposed within the bottom semi-circular portion of the micro-machined base enclosure, the cantilevers serve as a plurality of hair cells, wherein angular rotation of the hybrid MEMS microfluidic gyroscope creates an inertial force, which increases pressure on the cantilevers, leading to a detectable deflection that is proportional to the angular rotation.

The present invention also includes a hybrid MEMS microfluidic gyroscope that includes a single membrane disposed within the bottom semi-circular portion of the micro-machined base enclosure, wherein angular rotation of the hybrid MEMS microfluidic gyroscope creates an inertial force, which increases pressure on the single membrane, leading to a detectable deflection that is proportional to the angular rotation.

It is an object of the present invention to provide a hybrid MEMS microfluidic gyroscope that is well-suited for vestibular implants, due to reduced power consumption and increased reliability, by eliminating continually vibrating structures.

It is an object of the present invention to provide a hybrid MEMS microfluidic gyroscope that is based on a relatively large fluidic mass that deflects a sensing element similar in principle to a biological semicircular canal or SCC in contrast with one or more already existing gyroscopes that utilize vibrating structures as sensing elements.

It is an object of the present invention to provide a hybrid MEMS microfluidic gyroscope that eliminates the problems of power consumption and reliability of conventional gyroscopes.

BRIEF DESCRIPTION OF THE DRAWINGS

The present invention will be described by way of exemplary embodiments, but not limitations, illustrated in the accompanying drawings in which like references denote similar elements, and in which.

DETAILED DESCRIPTION OF ILLUSTRATIVE EMBODIMENTS

Various aspects of the illustrative embodiments will be described using terms commonly employed by those skilled in the art to convey the substance of their work to others skilled in the art. However, it will be apparent to those skilled in the art that the present invention may be practiced with only some of the described aspects. For purposes of explanation, specific numbers, materials and configurations are set forth in order to provide a thorough understanding of the illustrative embodiments. However, it will be apparent to one skilled in the art that the present invention may be practiced without the specific details. In other instances, well-known features are omitted or simplified in order not to obscure the illustrative embodiments.

Various operations will be described as multiple discrete operations, in turn, in a manner that is most helpful in understanding the present invention however the order of description should not be construed as to imply that these operations are necessarily order dependent. In particular, these operations need not be performed in the order of presentation.

The phrase "in one embodiment" is used repeatedly. The phrase generally does not refer to the same embodiment, however, it may. The terms "comprising", "having" and "including" are synonymous, unless the context dictates otherwise.

Figure 1:
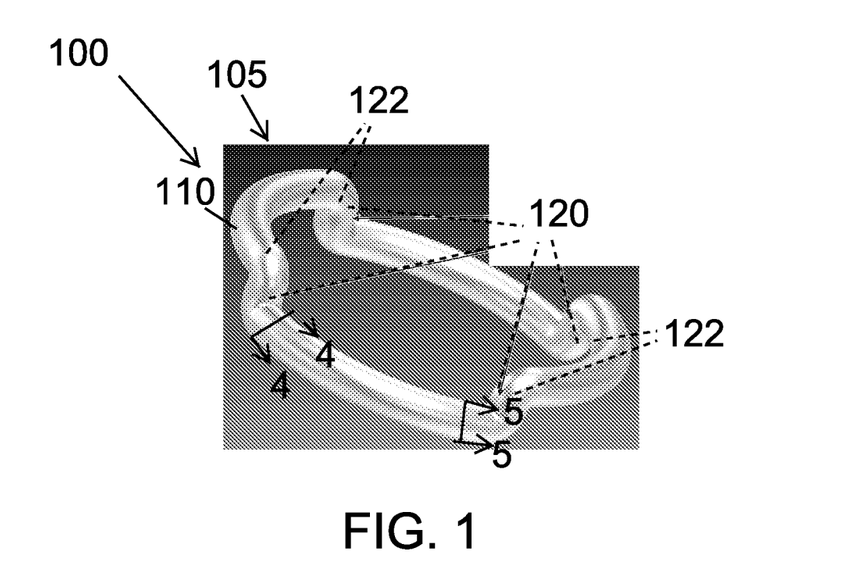
FIG. 1 illustrates an overhead perspective view of a first micro electro-mechanical system or MEMS gyroscope, in accordance with one embodiment of the present invention.

FIG. 1 illustrates an overhead perspective view of a first micro electro-mechanical system or MEMS gyroscope 100, in accordance with one embodiment of the present invention. The first MEMS gyroscope 100 may be utilized as an angular rate sensor in biomedical implants and typically in vestibular implants where power consumption and reliability may be of concern. The first MEMS gyroscope 100 may also be utilized in a wearable electronic sensor or any other suitable application or usage. The first MEMS gyroscope 100 may be a hybrid MEMS microfluidic gyroscope 105 or other suitable MEMS gyroscope.

The first MEMS gyroscope 100 may include a base enclosure 110 and a plurality of cantilevers 120. The base enclosure 110 may be bulk micro-machined or manufactured by any other suitable process. The base enclosure 110 may be made of silicon or any other suitable material. The base enclosure 110 may not necessarily be entirely made of the same material. The cantilevers 120 may serve as hair cells or other suitable type of sensory receptor. Angular rotation of the first MEMS gyroscope 100 may create an inertial force, which increases the pressure on the cantilevers 120, leading to a detectable deflection that is proportional to the angular rotation.

Figure 2:
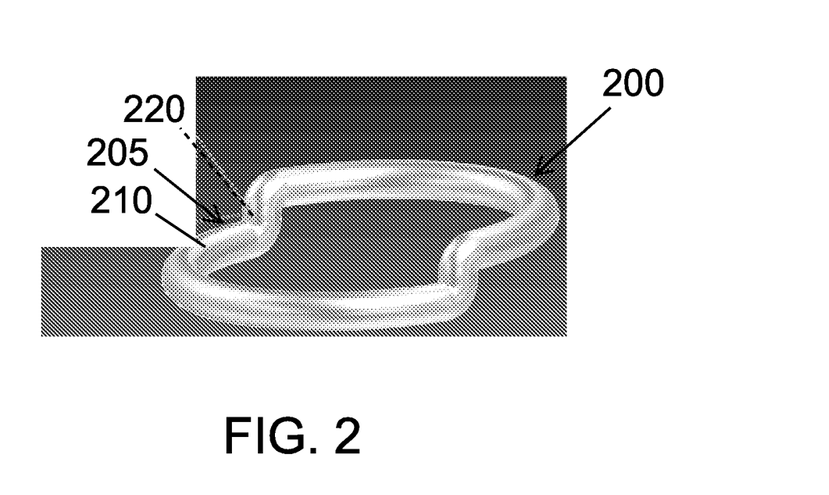
FIG. 2 illustrates an overhead perspective view of a second MEMS gyroscope, in accordance with one embodiment of the present invention.

FIG. 2 illustrates an overhead perspective view of a second MEMS gyroscope 200, in accordance with one embodiment of the present invention. The second MEMS gyroscope 200 may be utilized as an angular rate sensor in biomedical implants and typically in vestibular implants where power consumption and reliability may be of concern. The second MEMS gyroscope 200 may also be utilized in a wearable electronic sensor or any other suitable application or usage. The second MEMS gyroscope 200 may be a second hybrid MEMS microfluidic gyroscope 205 or other suitable type of gyroscope.

The second MEMS gyroscope 200 may include a base enclosure 210 and a single membrane 220. The base enclosure 210 may be bulk micro-machined or manufactured by any other suitable process. The base enclosure 210 may be made of silicon or any other suitable material. The single membrane 220 may serve as a sensory receptor. Angular rotation of the second MEMS gyroscope 200 may create an inertial force, which increases the pressure on the single membrane 220, leading to a detectable deflection that is proportional to the angular rotation.

Figure 3:
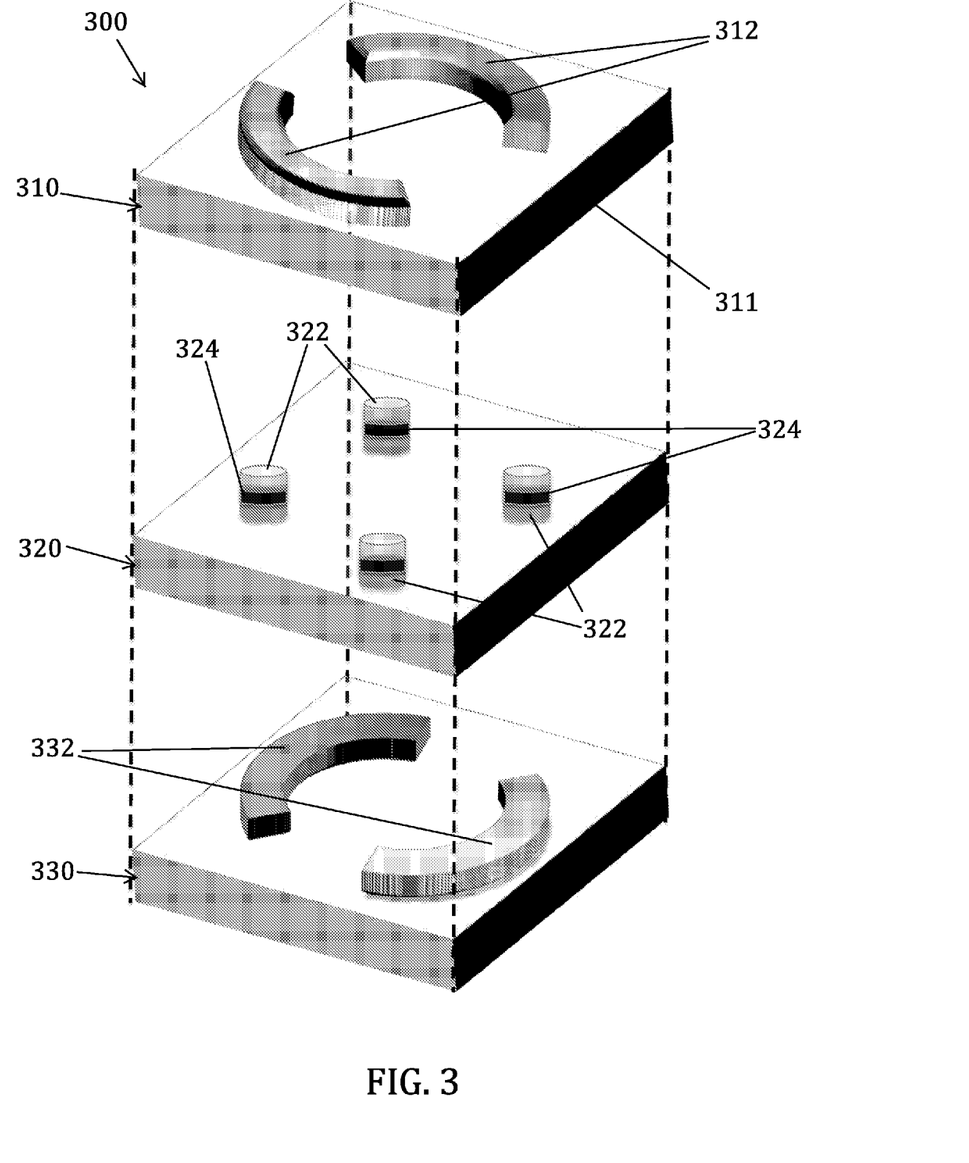
FIG. 3 illustrates an exploded perspective view of a first MEMS gyroscope, in accordance with one embodiment of the present invention.

FIG. 3 illustrates an exploded perspective view of a first MEMS gyroscope 300, in accordance with one embodiment of the present invention. The first MEMS gyroscope 300 may include a top fluid enclosure 310, a fluid sensing enclosure 320 and a bottom fluid enclosure 330.

The top fluid enclosure 310 may be constructed by partially etching or otherwise machining glass or any other suitable material, thereby creating a pair of discrete canals 312 on a bottom side 311 of the top fluid enclosure 310.

The fluid sensing enclosure 320 may be constructed from a layer of MEMS grade silicon or other suitable material which may be micro machined to include a sensing structure 324, which may be accessible to the fluid via an opening on either side of the fluid sensing enclosure 320.

The bottom fluid enclosure 330 may be constructed by partially etching or otherwise machining glass or any other suitable material, thereby creating two discrete canals 332 on the top side 331 of bottom fluid enclosure 330.

The top fluid enclosure 310, the fluid sensing enclosure 320 and the bottom fluid enclosure 330 may be hermetically bonded together utilizing an anodic bonding or other suitable technique, thereby forming a continuous fluid-filled closed shape that previously has been described as the base enclosure 110.

Figure 4:
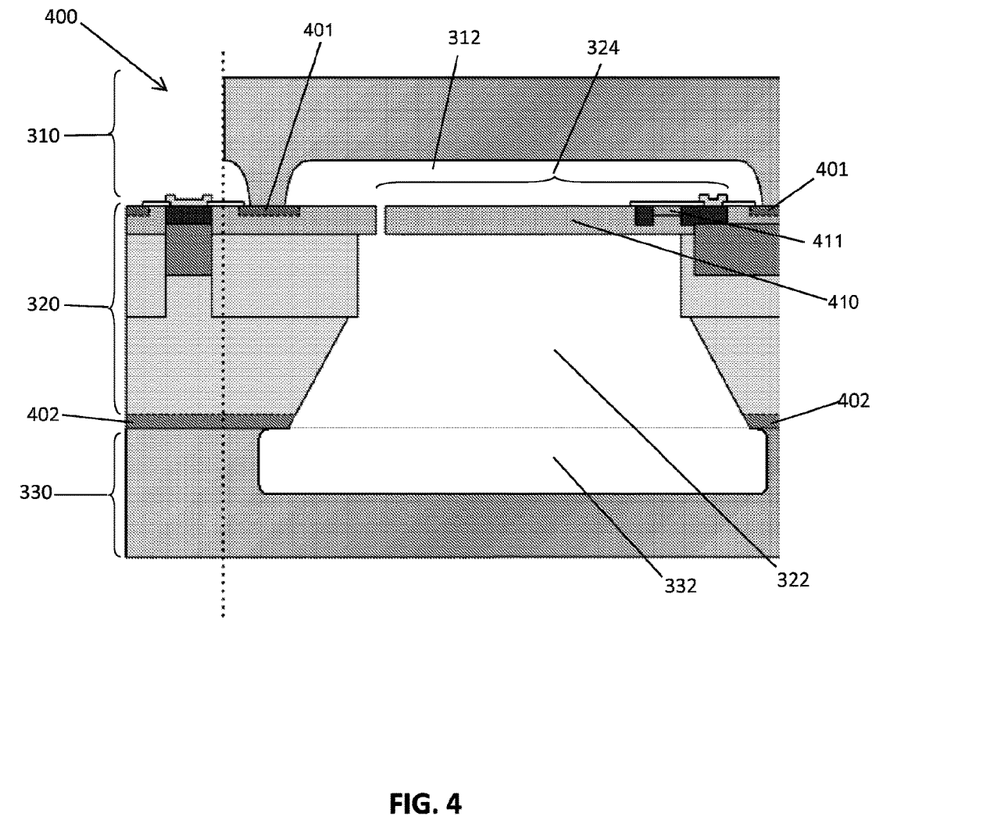
FIG. 4 illustrates a cross-sectional view of a first MEMS gyroscope along line 4-4 of FIG. 1, in accordance with one embodiment of the present invention.

FIG. 4 illustrates a cross-sectional view 400 of a first MEMS gyroscope along line 4-4 of FIG. 1, in accordance with one embodiment of the present invention. The top fluid enclosure 310 and the fluid sensing enclosure 320 may be anodically bonded to a cantilever 410.

The sensing structure 324 includes a cantilever 410 which may have a piezoresistor 411 embedded at the edge of the cantilever 410, where maximum stress and strain may occur. The pair of discrete canals 312 above the sensing structure 324 may be part of the top fluid enclosure 310. The fluid-filled void 322, below the sensing structure 324 communicates with the canal 332 on the top of bottom-fluid-enclosing structure 330. The fluidic mass that fills the entire base enclosure 110 may be any suitable high-density, low-viscosity and non-toxic fluid such as sodium polytungstate liquid or water that achieves an angular rate sensitivity similar to that of a healthy human. The fluidic mass in the first MEMS gyroscope may be free to flow in the pair of discrete canals 312 of the top fluid enclosing structure 310, through the openings of the fluid sensing structure 320, past the cantilever sensing structure and into and around the canals 332 of the bottom-fluid-enclosing structure 330. The piezo-resistors 411 may serve as piezoresistive strain gauges that may be strategically located at regions of maximum stress, which may be at the perimeter edges thereby giving maximum electrical sensitivity. The piezo-resistors 411 may be deformed by the movement of the fluidic mass. The fluidic mass may prevent gravitational forces that may be exerted onto the first MEMS gyroscope 300 from deflecting the piezo-resistors 411. FIG. 3 illustrates four cantilever sensing structures 324 disposed within the fluid sensing structure 320 as this may be suitable for constructing a Wheatstone bridge however any suitable number of cantilevers 410 may be disposed within the sensing structure 320.

Figure 5:
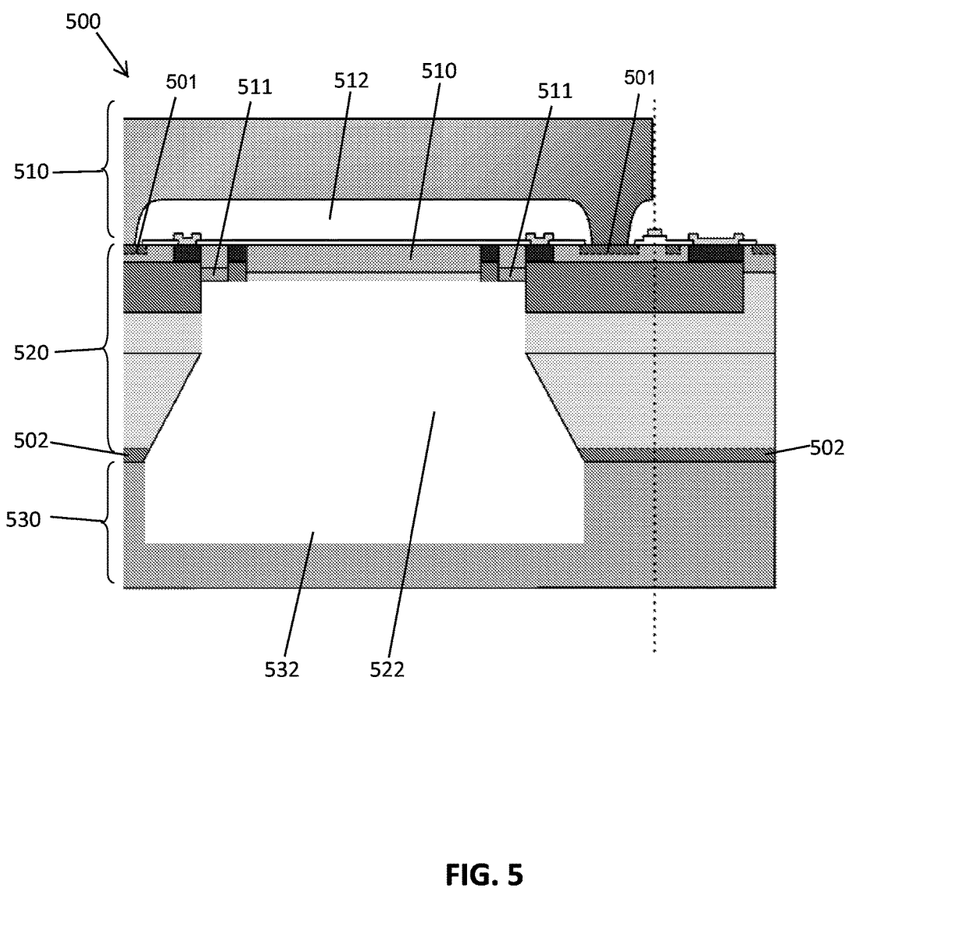
FIG. 5 illustrates a cross-sectional view of a second MEMS gyroscope along line 5-5 of FIG. 2, in accordance with one embodiment of the present invention.

FIG. 5 illustrates a cross-sectional view of a second MEMS gyroscope 500 along line 5-5 of FIG. 2, in accordance with one embodiment of the present invention. The second MEMS gyroscope 500 may be utilized to detect fluid motion.

The second MEMS gyroscope 500 may include a base enclosure 210, a top fluid enclosure 510, a fluid sensing enclosure 520 and a bottom fluid enclosure 530. The top fluid enclosure 510 may be constructed by partially etching or machining glass or any other suitable material, thereby creating a single top fluid canal 512 on a bottom side of the top fluid enclosure 510. The fluid sensing enclosure 520 may be constructed from a layer of MEMS grade silicon or other suitable material, which may be micro machined to include a circular sensing diaphragm 510', which is accessible to fluid on either side of the second MEMS gyroscope 500. The bottom fluid enclosure 530 may be constructed by partially etching or otherwise machining glass or other suitable material, thereby creating a canal 532 on a top side of the bottom fluid enclosure 530. The top fluid enclosure 510, the fluid sensing enclosure 520 and the bottom fluid enclosure 530 may be hermetically bonded together utilizing an anodic bonding or other suitable technique, thereby forming a continuous fluid filled closed shape with a circular sensing diaphragm 510' as outlined in FIG. 2. The circular sensing diaphragm 510' has four piezoresistors 411 embedded at the edges, where it may be subjected to maximum stress and strain. The orientation may be such that under pressure, a pair of the piezoresistors 411 may exhibit compressive stress, while the other pair of the piezoresistors 411 may exhibit tensile stress, thereby enabling construction of a Wheatstone bridge. As illustrated in FIG. 5, to maximize the sensitivity however any number of intercepting membranes may be built.

Figure 6:
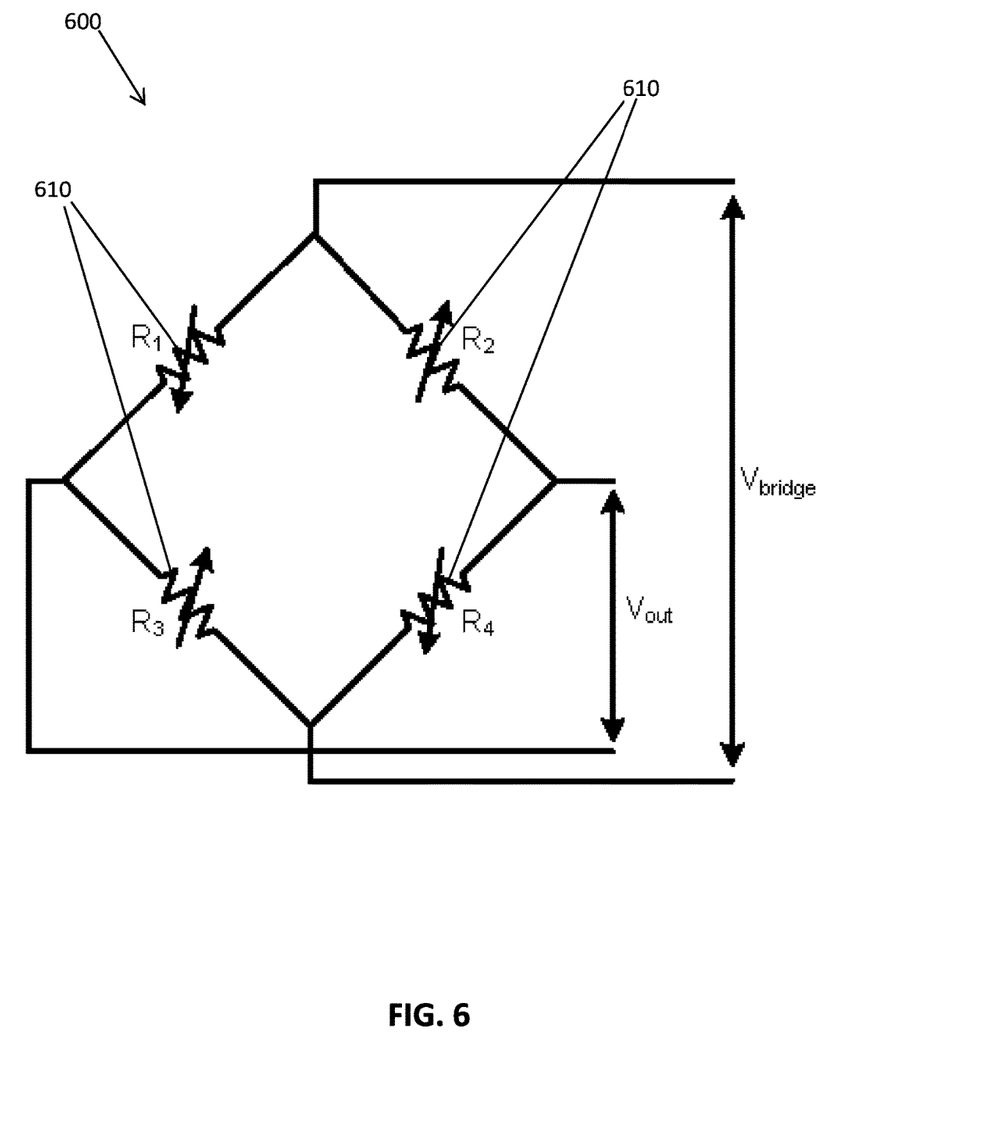
FIG. 6 illustrates an electrical schematic of a Wheatstone bridge, in accordance with one embodiment of the present invention.

FIG. 6 illustrates an electrical schematic of a Wheatstone bridge 600, in accordance with one embodiment of the present invention.

The Wheatstone bridge 600 may include a plurality of piezo-resistors 610. The piezo-resistors 610 may be designed in pairs, either within different sensing structures as illustrated in the case of FIG. 3, or within the same sensing structure as described in the case of a circular sensing diaphragm.

A differential read-out circuit then may eliminate the effects of process variations. The piezo-resistors 610 may be placed longitudinally and two transversally to the stress axes, oriented parallel and perpendicular to the 110 crystallographic direction, in order to maximize the coefficients of piezo-resistivity. During angular motion, in each resistive divider leg, one piezo-resistor 610 may undergo compressive stress, while the other may undergo tensile stress. Thereby the two resistive divider legs will determine the output voltage as shown in the equation below:

$$\Delta V_{out} \propto \Delta R \propto \Pi_L \sigma_L + \Pi_T \sigma_T \propto \Pi(P-P_o). \quad (2)$$

where $\pi$ is the piezoresistive coefficient, a is the mechanical stress, subscripts L & T denote the longitudinal and transversal coefficients respectively, along the resistor axes, and (P–Po) is the differential pressure on the sensing element. The thickness of the silicon membrane-cantilever is approximately 3.1±0.3 μm or other suitable thickness. The output voltage of the Wheatstone bridge utilized in the proposed structures of FIGS. 1 and 2 are described by the equation below.

$$V_{out} = V_{EXC}\left(\frac{R_3}{R_1+R_3} - \frac{R_4}{R_2+R_4}\right)$$

Figure 7:
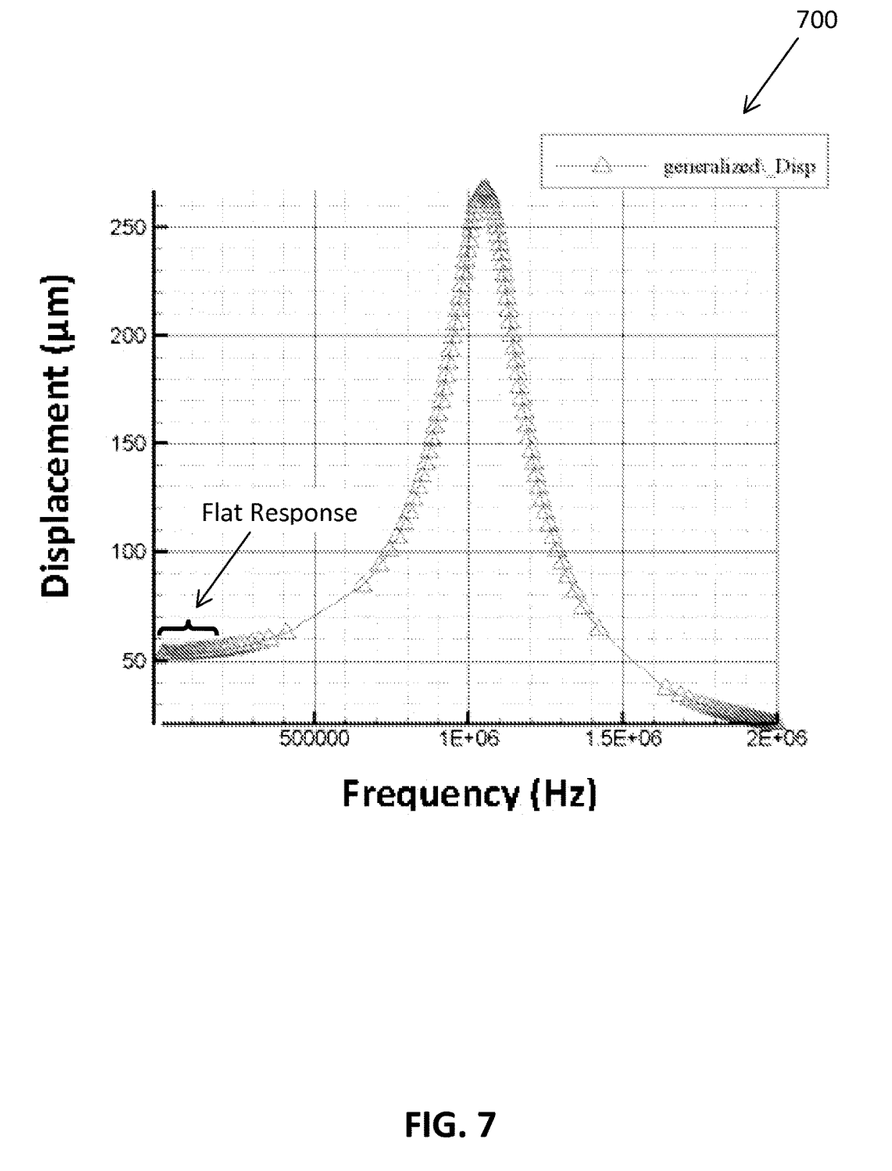
FIG. 7 illustrates a graph of a frequency response of a first hybrid MEMS microfluidic gyroscope, in accordance with one embodiment of the present invention.

FIG. 7 illustrates a graph 700 of a frequency response of a first hybrid MEMS microfluidic gyroscope, in accordance with one embodiment of the present invention.

The graph 700 illustrates a flat response at the frequencies of interest, i.e. in the range of approximately 0 Hz to 1.5 Hz. Furthermore, the resonant frequencies of the cantilever structure are well beyond this range, being approximately 1.05 MHz and approximately 0.22 MHz respectively.

Figure 8:
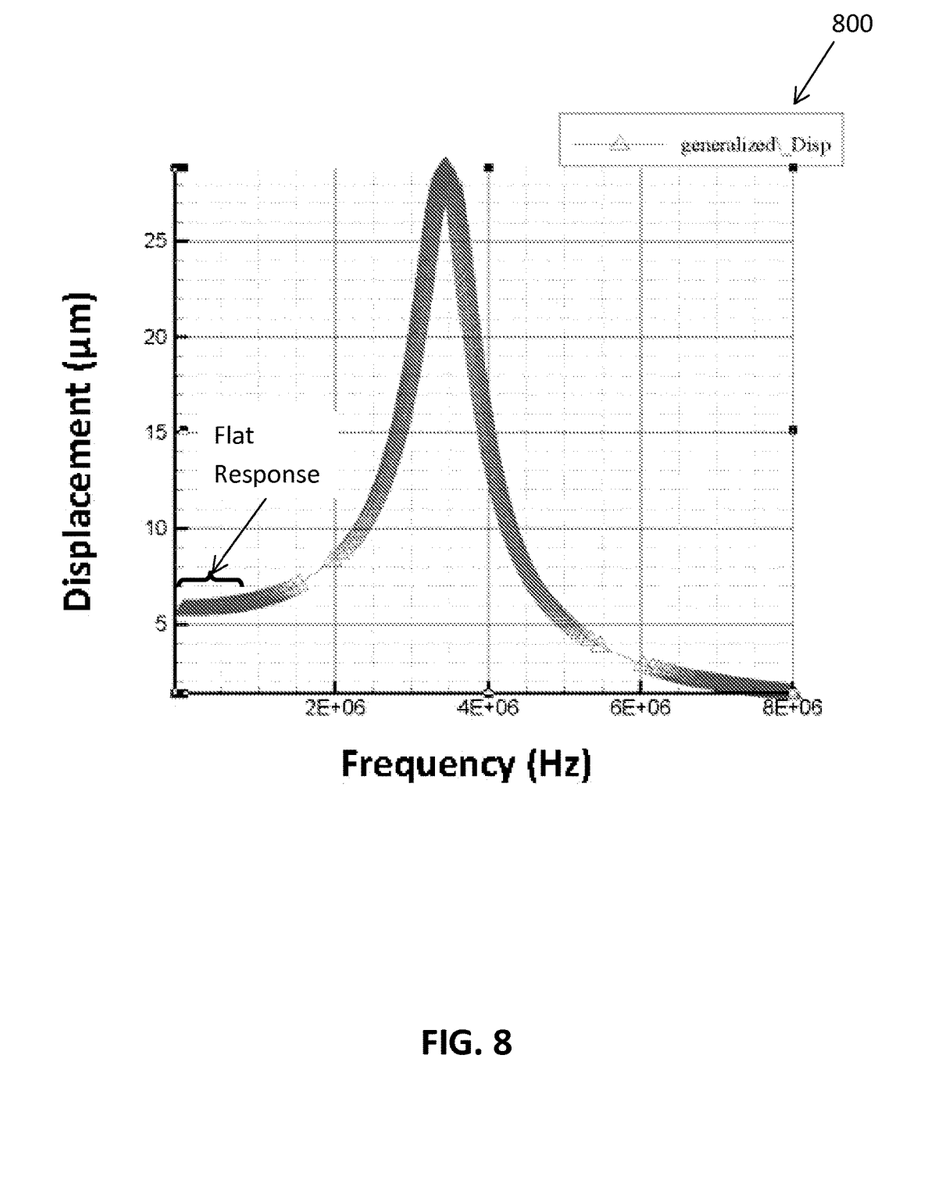
FIG. 8 illustrates a graph of a frequency response of a second hybrid MEMS microfluidic gyroscope, in accordance with one embodiment of the present invention.

FIG. 8 illustrates a graph 800 of a frequency response of a second hybrid MEMS microfluidic gyroscope, in accordance with one embodiment of the present invention.

The graph 800 illustrates a flat response at the frequencies of interest, i.e.

in the range of approximately 0 Hz to 1.5 Hz. Furthermore, the resonant frequencies of the cantilever structure are well beyond this range, being approximately 1.05 MHz and approximately 0.22 MHz respectively.

The MEMS gyroscopes may be intended to be utilized as an angular rate sensor in biomedical implants and mostly in vestibular implants where power consumption and reliability are of major concern. The MEMS gyroscope may also be utilized in wearable electronic sensors. By choosing a high-density, low-viscosity and non-toxic fluid, a high angular-rate sensitivity may be achieved, that exceeds that of humans. Furthermore a thin enough sensing element may achieve high sensitivities. The MEMS gyroscopes may utilize a fluidic mass that may be contained in etched glass layers, which may be anodically bonded on top and below of a bulk micro-machined silicon layer, and whose deflectable structures contain buried piezo-resistors for sensing. In one embodiment, the deflectable structures may include four cantilevers, one in each cross-section of the upper and lower levels of the channel, which may serve as the hair cells of the semi-circular canal or SCC.

In another embodiment of the present invention, the deflectable structure may be a membrane. The membrane may increase the inertial mass and the sensitivity of the system without utilizing the Coriolis affect. The fact that a fluid may be utilized for the larger mass means that gravitational forces do not affect the sensor (as would be the case with a large solid mass suspended on a thin beam) and the device may easily handle a deceleration or acceleration of five thousand g's (1 g=9.8 m/s$^2$), which is typical in a drop test. Angular rotation of the whole device may create an inertial force, which may increase the pressure on the sensing membrane or the cantilever (hair cell), leading to a detectable deflection that is proportional to the angular rotation. The sensing piezoresistive strain gauges may be strategically located at regions of maximum stress a, which may be at the perimeter edges of the cantilever/membrane, to give increased electrical sensitivity. To cope with process variations, strain gauges may be designed in pairs, to form a Wheatstone bridge, which converts the strain induced resistance variations into output voltage variations. A differential read-out circuit then may eliminate the effects of process variations. In FIGS. 1 and 2, two of the piezo-resistors are placed longitudinally and two transversally to the stress axes, oriented parallel and perpendicular to the 110 crystallographic direction, in order to maximize the coefficients of piezo-resistivity. During angular motion, in each resistive divider leg, one piezo-resistor undergoes compressive stress, while the other undergoes tensile stress. Thereby the two resistive divider legs may determine the output voltage. The two different structures, one with a sensing cantilever and another with a sensing membrane may be fabricated on two different dies in one of Sensonor's MEMS technologies.

While the present invention has been related in terms of the foregoing embodiments, those skilled in the art will recognize that the invention is not limited to the embodiments described. The present invention can be practiced with modification and alteration within the spirit and scope of the appended claims. Thereby, the description is to be regarded as illustrative instead of restrictive on the present invention.

What is claimed is:

1. A hybrid MEMS microfluidic gyroscope, comprising:
   a micro-machined base enclosure having a top fluid enclosure, a fluid sensing enclosure and a bottom fluid enclosure, the top fluid enclosure defining a pair of discrete canals on a bottom side of the top fluid enclosure, the fluid sensing enclosure including a sensing structure, which is accessible to a fluid via an opening on either side of the fluid sensing enclosure and the bottom fluid enclosure including glass that defines two discrete canals on a top side of the bottom fluid enclosure;
   a plurality of piezo-resistors disposed within the micro-machined base enclosure, the piezo-resistors is deformed by the fluid, the fluid prevents gravitational forces asserted onto the hybrid MEMS microfluidic gyroscope from affecting the piezo-resistors; and
   a plurality of cantilevers disposed within the micro-machined base enclosure, the cantilevers serve as a plurality of hair cells, wherein angular rotation of the hybrid MEMS microfluidic gyroscope creates an inertial force, which increases pressure on the cantilevers, leading to a detectable deflection that is proportional to the angular rotation.

2. The hybrid MEMS microfluidic gyroscope according to claim 1, wherein the fluid sensing enclosure is constructed from a layer of MEMS grade silicon.

3. The hybrid MEMS microfluidic gyroscope according to claim 1, wherein the fluid sensing enclosure is anodically bonded to other fluid enclosing structures.

4. The hybrid MEMS microfluidic gyroscope according to claim 1, wherein the fluid is a high-density, low-viscosity and non-toxic fluid that achieves a high angular rate sensitivity.

5. The hybrid MEMS microfluidic gyroscope according to claim 4, wherein the high-density, low-viscosity and non-toxic fluid is sodium polytungstate liquid.

6. The hybrid MEMS microfluidic gyroscope according to claim 4, wherein the high-density, low-viscosity and non-toxic fluid is water with or without a soluble material.

7. The hybrid MEMS microfluidic gyroscope according to claim 1, wherein the piezo-resistors serve as piezoresistive strain gauges that are located at perimeter edges of the cantilevers to give increased electrical sensitivity.

8. The hybrid MEMS microfluidic gyroscope according to claim 1, wherein the hybrid MEMS microfluidic gyroscope is utilized as an angular rate sensor in a biomedical implant.

9. The hybrid MEMS microfluidic gyroscope according to claim 8, wherein the biomedical implant is a vestibular implant where power consumption and reliability is of concern.

10. The hybrid MEMS microfluidic gyroscope according to claim 1, wherein the hybrid MEMS microfluidic gyroscope is utilized in a wearable electronic sensor.

* * * * *